United States Patent [19]

Mayclin

[11] 4,439,154

[45] Mar. 27, 1984

[54] PERMANENT IDENTIFICATION METHOD FOR REMOVABLE DENTAL PROSTHESIS AND STRUCTURE

[76] Inventor: Thomas J. Mayclin, 5705 Dale Ave., Edina, Minn. 55436

[21] Appl. No.: 282,543

[22] Filed: Jul. 13, 1981

[51] Int. Cl.³ .............................................. A61C 13/00
[52] U.S. Cl. ...................................... 433/229; 433/203
[58] Field of Search ............... 433/203, 215, 229, 199; 264/17

[56] References Cited

U.S. PATENT DOCUMENTS

| | | | |
|---|---|---|---|
| 3,431,330 | 3/1969 | Cornell | 264/17 |
| 3,503,127 | 3/1970 | Kasdin et al. | 433/199 |
| 4,027,391 | 6/1977 | Samis | 433/229 |
| 4,208,795 | 6/1980 | Muhlemann | 433/203 |

FOREIGN PATENT DOCUMENTS

8205  7/1879  Fed. Rep. of Germany ...... 433/203

Primary Examiner—Robert Peshock
Attorney, Agent, or Firm—Henderson & Sturm

[57] ABSTRACT

The invention relates to a method to assist in identification of removable dental prosthesis or appliances which have an area of acrylic, vinyl or other plastic type material in which the carrier on which identifying information such as: name, Social Security number, address, telephone number or any combination thereof is imprinted can be embedded in and covered with a clear material of the same type or compatible with the original material of the dental prosthesis.

9 Claims, No Drawings

PERMANENT IDENTIFICATION METHOD FOR REMOVABLE DENTAL PROSTHESIS AND STRUCTURE

BACKGROUND OF THE INVENTION

1. Field of the Invention

The present invention relates to a method and structure for permanent and positive identification of removable dental prosthesis that have an area of ½"×½" or more of dental acrylic, vinyl or other type of plastic approved for use in mouth in which a carrier of identifying information can be embedded.

Carrier of identifying information can also be imbedded in ear molds for the hearing impaired. The carrier of identifying information can also be attached to optical eyewear, external hearing aids, and external medical devices, which if lost or misplaced can be returned to owner by means of identifying information on the carrier attached to item.

2. Description of Prior Art

Identification of removable dental prosthesis is presently being done by typing the name of the wearer on onion skin paper and embedding it in the denture. Onion-skin is fragile and hard to lay out flat which can result in a distorted image because of wrinkling or tearing during processing. Thin metal "shim" stock on which the name is typed using the "stencil" setting which in effect makes an engraved name in metal is another method used. The legibility of this type of identification and the disfigurement of the aesthetics of the dental prosthesis makes this form a less desirable method. External marking by roughing the surface, writing the name on the prosthesis with an indelible or water-proof marker and then sealing with a clear sealer is for temporary identification only and by no means a desirable method. Engraving with an engraving tool creates a rough surface for the tongue or tissues of the mouth and will also wear down with mastication of food and therefore is not desirable or practical.

In view of the size of the plastic area to embed a typewritten name and/or Social Security number or other identifying information on onion skin or a metal plate, and the distraction and distortion factor of the embedded methods now used, and with the lack of permanence of external marking, there is obviously a need for a small but legible and identifiable means or permanent identification of removable dental prosthesis.

Two states, Minnesota and Montana presently have state laws mandating identification of new dentures and removable dental prosthesis. Illinois has passed a similar act and, if signed by the Governor, will become law.

SUMMARY OF THE INVENTION

It is the aim of the present invention to provide a permanent method of identification of all removable dental prosthesis with a size of print that is one-half the size of typewritten letters thus making it more compact and concise and yet very legible and causing less distraction from the aesthetics of the appliance. It is an aim of the invention to provide the finder of a lost or misplaced dental appliance legible information by which the owner may be found.

The carrier which is an inert material, oriented styrene or other shrink type material, with a buffed or matte finish on which the information is typed or hand lettered and which after reduction in size by a dry heat method is embedded in a slot prepared or cured just beneath the surface of the denture. The reduced size of the carrier containing the 9 digits of a Social Security number and spaces between the sets of numbers for a total of 11 spaces and assuming the first name or initials plus last name of the person total eleven spaces the overall dimensions of the carrier are as follows: four (4) millimeters high, nine (9) millimeters long and one (1) millimeter thick. The size of the carrier which contains the essential information for tracing the ownership of the appliance can be embedded in any dental appliance with an area of six (6) millimeters high by eleven (11) millimeters long by two (2) millimeters in thickness of plastic, acrylic, vinyl or other dental type plastics. The legibility of the printing on the carrier is sufficient for persons with normal vision to read easily and yet does not distract from the aesthetics of the dental appliance.

The reduced carrier may also be embedded or processed in customer ear molds for hearing impaired persons for identification purposes using the same procedures as in dental appliance identification procedures. Gluing the identifying carrier to the exterior of the hearing aid using cyanoacrylate adhesive and then sealing the surface with a coat of the same adhesive would also aid in retrieving a lost or misplaced device. The same holds true for eyeglass wearers and other people who have external medical devices which if lost or misplaced would represent a substantial financial loss.

The carrier material, oriented styrene or other types of shrink material with a reduction factor of 50% is furnished to the dentist, dental laboratory or person doing the identifying in strip form. The carrier material will have a matte or buff surface on one side that will allow typewriter ink to print on it or accept hand lettered words using a fine-tip water-proof marker. For convenience sake, strips may also be furnished in ⅜ inch high by 1½ inch long pieces adhesively mounted to a paper back for ease of lettering and removal for use.

Once the identifying information is placed on the carrier material and verified for accuracy the excess material is trimmed from the carrier material leaving a border of approximately one (1) millimeter around the printed material. Ordinary scissors may be used to cut the material. Pinking scissors may be used for a notched affect of the border if the operator so desires. The notched border has the advantage of more surface area for the clear overlay material to adhere to. When the carrier material is trimmed it is ready to be reduced in size and there are several methods that can be used and they will be listed for inclusion in the process and then the preferred method will be elaborated on. Methods included are to hold over open flame with a tweezers and when carrier is reduced to smallest size place on heat resistant surface and flatten with heat resistant pad. Placing the carrier material on a metal sheet, preferrably with a non-stick surface and placing in a kitchen type oven at 275° to 500° Fahrenheit will reduce the carrier. A dry heat sterilizer such as used in a dental or medical office will work. Using heated sand or glass beads in the temperature range of 275° to 500° Fahrenheit will also work. Any oven or dry heating apparatus used in a dental, medical, optical, or ear mold manufacturing office or laboratory that allows a heat control in the range of 275° to 500° Fahrenheit will reduce the carrier.

A household toaster oven is the preferred appliance because of its compact size, rapid heat rise, energy efficiency and ease of operation. The removable tray should be sprayed with a silicone non-stick spray to prevent carrier material from sticking to tray during heating. The carrier material is placed on the lubricate tray printed side down and covered with a light metal sheet or heat resistant non-asbestos sheet, this is to allow the material to curl slightly while shrinking but provide enough weight so the carrier material will end up flat. At 400° Fahrenheit it takes approximately two (2) minutes for the carrier material to shrink completely. Once reduced, the tray is removed and allowed to cool and the carrier material is removed from tray. The carrier material surface on which the lettering appears, must then be sealed so the lettering does not release during processing. A liquid acrylic polish, varnish or sealer is used as a coating to protect lettering during processing. The carrier material is now ready to be processed in the denture by commonly accepted practices used for processing new dentures or processed in an existing dental prosthesis by commonly accepted methods.

I claim:

1. An identification method adapted for use in removable dental prosthesis comprising the steps of:
   forming a recessed slot in a section of said dental prosthesis;
   transcribing written information on the surface of an information carrier film, said information carrier film being an inert, heat shrinkable film;
   applying heat to said information carrier film to reduce the surface area of said film and to reduce the size of said written information carried on said film;
   placing the reduced information carrier film in said recessed slot; and
   covering said information carrier film with a clear overlay material compatible with the material of said dental prosthesis.

2. The identification method of claim 1 wherein said information carrier film is oriented styrene which shrinks fifty percent (50%) in each direction for distortion free reduction when said heat is applied.

3. The identification method of claim 2 wherein said written information is typed, lettered, or written on the flat buffed or matte surface of said information carrier film and said written information is reduced fifty percent (50%) in size when said heat is applied.

4. The identification method of claim 1 wherein said recessed slot is rectangular in shape.

5. The identification method of claim 1 wherein said information carrier film includes an adhesive backing that is removed after the written information is transcribed and before heat is applied to reduce the size.

6. The identification method of claim 1 further including the step of trimming excess material from the borders of said information carrier film before applying heat to reduce the size.

7. The identification method of claim 6 wherein said trimming step includes trimming the borders in a zigzag pattern to increase the surface area to which the clear overlay material will adhere.

8. The identification method of claim 1 further including the step of coating the surface of the information carrier film to protect the written information after said heat is applied.

9. The identification method of claim 8 wherein said coating step includes applying a coating selected from a group consisting of liquid acrylic polish, varnish and sealer, and cyanoacrylate.

* * * * *